United States Patent
Alhudaib et al.

(10) Patent No.: US 11,812,751 B1
(45) Date of Patent: Nov. 14, 2023

(54) BIOCONTROL AGENTS FOR USE AGAINST SOIL AND AIR-BORNE FUNGAL PATHOGENS

(71) Applicant: KING FAISAL UNIVERSITY, Al-Ahsa (SA)

(72) Inventors: Khalid A. Alhudaib, Al-Ahsa (SA); Sherif Mohamed El-Ganainy, Al-Ahsa (SA); Muhammad Naeem Sattar, Al-Ahsa (SA); Mustafa Ibrahim Al-Maghaslah, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 17/937,759

(22) Filed: Oct. 3, 2022

(51) Int. Cl.
   *A01N 63/38* (2020.01)

(52) U.S. Cl.
   CPC .................................. *A01N 63/38* (2020.01)

(58) Field of Classification Search
   CPC ........... C12N 1/14; C12N 1/145; A01N 63/38
   See application file for complete search history.

(56) References Cited

U.S. PATENT DOCUMENTS

| 2004/0151698 A1 | 8/2004 | Chung et al. |
| 2011/0214464 A1 | 9/2011 | Shen et al. |
| 2022/0039394 A1* | 2/2022 | Hübsch .................. A01N 61/00 |

FOREIGN PATENT DOCUMENTS

| CN | 101637188 A | 2/2010 | |
| CN | 103772000 A | 5/2014 | |
| CN | 109730079 A | 5/2019 | |
| CN | 111807893 A | 10/2020 | |
| CN | 113234635 A | 8/2021 | |
| WO | WO-2020126567 A1 * | 6/2020 | ............... A01G 7/06 |

OTHER PUBLICATIONS

GenBank Trichoderma harzianum, 2020 (Year: 2020).*
GenBank Trichoderma longibrachiatum, 2020 (Year: 2020).*
GenBank Trichoderma asperellum, 2020 (Year: 2020).*
Al-Naemi, F. A., et al., "Antagonistic Effects of Trichoderma harzianum Isolates against Ceratocystis radicicola: pioneering a Biocontrol Strategy against Black Scorch Disease in Date Palm Trees," Journal of Phytopathology, vol. 164, Issue 7-8, Aug. 2016, pp. 464-475.

* cited by examiner

*Primary Examiner* — Ruth A Davis
(74) *Attorney, Agent, or Firm* — Nath, Goldberg & Meyer; Richard C. Litman

(57) ABSTRACT

The biocontrol agent for use against soil and air-borne pathogens includes a mixture of isolates from at least three *Trichoderma* species, including *Trichoderma harzianum*, *Trichoderma longibrachiatum*, and *Trichoderma asperellum*. The mixture of *Trichoderma* isolates may be effective in controlling plant pathogens. The biocontrol agent for use against soil and air-borne fungal pathogens may be formulated as a wettable powder. The biocontrol agent may be used in the treatment or prevention of infection of date palms with *Thielaviopsis punctulata*. In a further embodiment, the biocontrol agent may be used in the treatment or prevention of infection of cucumbers with *Rhizoctonia solanii*.

18 Claims, No Drawings

Specification includes a Sequence Listing.

SEQUENCE LISTING

```
Sequence total quantity: 5
SEQ ID NO: 1            moltype = DNA  length = 409
FEATURE                 Location/Qualifiers
source                  1..409
                        mol_type = genomic DNA
                        organism = Trichoderma longibrachiatum
SEQUENCE: 1
cccaaacccc aatgtgaacg ttaccaatct gttgcctcgg cgggattctc ttgccccggg   60
cgcgtcgcag ccccggatcc catggcgccc gccggaggac caactccaaa ctcttttttc  120
tctccgtcgc ggctcccgtc gcggctctgt tttatttttg ctctgagcct ttctcggcga  180
ccctagcggg cgtctcgaaa atgaatcaaa actttcaaca acggatctct tggttctggc  240
atcgatgaag aacgcagcga aatgcgataa gtaatgtgaa ttgcagaatt cagtgaatca  300
tcgaatcttt gaacgcacat tgcgcccgcc agtattctgg cgggcatgcc tgtccgagcg  360
tcatttcaac cctcgaaccc ctccgggggg tcggcgttgg ggatcggcc               409

SEQ ID NO: 2            moltype = DNA  length = 569
FEATURE                 Location/Qualifiers
source                  1..569
                        mol_type = genomic DNA
                        organism = Trichoderma asperellum
SEQUENCE: 2
cattaccgag tttacaactc ccaaacccaa tgtgaacgtt accaaactgt tgcctcggcg   60
gggtcacgcc ccgggtgcgt cgcagccccg gaaccaggcg cccgccggag gaaccaacca  120
aactctttct gtagtcccct cgcggacgta tttctttaca gctctgagca aaaattcaaa  180
atgaatcaaa actttcaaca acggatctct tggttctggc atcgatgaag aacgcagcga  240
aatgcgataa gtaatgtgaa ttgcagaatt cagtgaatca tcgaatcttt gaacgcacat  300
tgcgcccgcc agtattctgg cgggcatgcc tgtccgagcg tcatttcaac cctcgaaccc  360
ctccggggga tcggcgttgg ggatcgggac ccctcacacg ggtgccggcc cctaaataca  420
gtggcggtct cgccgcagcc tctcctgcgc agtagtttgc acaactcgca ccgggagcgc  480
ggcgcgtcca cgtccgtaaa acacccaact ttctgaaatg ttgacctcgg atcaggtagg  540
aatacccgct gaacttaagc atatcataa                                    569

SEQ ID NO: 3            moltype = DNA  length = 595
FEATURE                 Location/Qualifiers
source                  1..595
                        mol_type = genomic DNA
                        organism = Trichoderma asperellum
```

```
SEQUENCE: 3
tccgtaggtg aacctgcgga gggatcatta ccgagtttac aactcccaaa cccaatgtga   60
acgttaccaa actgttgcct cggcggggtc acgccccggg tgcgtcgcag ccccggaacc  120
aggcgcccgc cggaggaacc aaccaaactc tttctgtagt ccctcgcgg acgtatttct  180
ttacagctct gagcaaaaat tcaaaatgaa tcaaaacttt caacaacgga tctcttggtt  240
ctggcatcga tgaagaacgc agcgaaatgc gataagtaat gtgaattgca gaattcagtg  300
aatcatcgaa tctttgaacg cacattgcgc ccgccagtat tctggcgggc atgcctgtcc  360
gagcgtcatt tcaaccctcg aacccctccg ggggatcggc gttggggatc gggaccccctc  420
acacgggtgc cggcccctaa atacagtggc ggtctcgccg cagcctctcc tgcgcagtag  480
tttgcacaac tcgcaccggg agcgcggcgc gtccacgtcc gtaaaacacc caactttctg  540
aaatgttgac ctcggatcag gtaggaatac ccgctgaact taagcatatc aataa       595

SEQ ID NO: 4        moltype = DNA  length = 538
FEATURE             Location/Qualifiers
source              1..538
                    mol_type = genomic DNA
                    organism = Trichoderma harzianum
SEQUENCE: 4
gggatcatta ccgagtttac aactcccaaa cccaatgtga acgttaccaa actgttgcct   60
cggcgggatc tctgccccgg gtgcgtcgca gccccggacc aaggcgcccg ccggaggacc  120
aaccaaaact cttattgtat acccctcgc gggttttttt tataatctga gccttctcgg  180
cgcctctcgt aggcgtttcg aaaatgaatc aaaactttca caacggatc tcttggttct  240
ggcatcgatg aagaacgcag cgaaatgcga taagtaatgt gaattgcaga attcagtgaa  300
tcatcgaatc tttgaacgca cattgcgccc gccagtattc tggcgggcat gcctgtccga  360
gcgtcatttc aaccctcgaa cccctccggg gggtcggcgt tggggatcgg ccctgccttg  420
gcggtggccg tctccgaaat acagtggcgg tctcgccgca gcctctcctg cgcagtagtt  480
tgcacactcg catcgggagc gcggcgcgtc cacagccgtt aaacacccaa cttctgaa   538

SEQ ID NO: 5        moltype = DNA  length = 643
FEATURE             Location/Qualifiers
source              1..643
                    mol_type = genomic DNA
                    organism = Trichoderma harzianum
SEQUENCE: 5
ggaagtaaaa gtcgtaacaa ggtctccgtt ggtgaaccag cggagggatc attaccgagt   60
ttacaactcc caaacccaat gtgaacgtta ccaaactgtt gcctcggcgg gatctctgcc  120
ccggggtgcgt cgcagccccg gaccaaggcg cccgccggag gaccaaccaa aactcttatt  180
gtataccccc tcgcgggttt tttttataat ctgagccttc tcggcgcctc tcgtaggcgt  240
ttcgaaaatg aatcaaaact ttcaacaacg gatctcttgg ttctggcatc gatgaagaac  300
gcagcgaaat gcgataagta atgtgaattg cagaattcag tgaatcatcg aatctttgaa  360
cgcacattgc gcccgccagt attctggcgg gcatgcctgt ccgagcgtca tttcaaccct  420
cgaacccctc cgggggtcg gcgttgggga tcggccctgc cttggcggtg gccgtctccg  480
aaatacagtg gcggtctcgc cgcagcctct cctgcgcagt agtttgcaca ctcgcatcgg  540
gagcgcggcg cgtccacagc cgttaaacac ccaacttctg aaatgttgac ctcggatcag  600
gtaggaatac ccgctgaact taagcatatc aataagcgga gga                   643
```

BIOCONTROL AGENTS FOR USE AGAINST SOIL AND AIR-BORNE FUNGAL PATHOGENS

SEQUENCE LISTING XML

The instant application contains a Sequence Listing XML, which has been submitted in XML format via the USPTO's Patent Center and is hereby incorporated by reference in its entirety. The XML copy, created on Aug. 15, 2022, is named 32087_61U_Seq.xml and is 8,000 bytes in size.

BACKGROUND

1. Field

The disclosure of the present patent application relates to biocontrol agents for use against soil and air-borne fungal pathogens, and particularly to a mixture of *Trichoderma* species formulated as a wettable powder for use as a biopesticide.

2. Description of the Related Art

Plant diseases are a primary threat impacting the ability of farmers to produce consistent crop yields. Plants may fall ill to many diseases, including various fungal pathogens. Common plant fungal diseases are caused by sclerotia residing in the soil and causing a broad spectrum of crop diseases. Traditional methods of managing plant pathogens have involved using chemical pesticides, which are potentially harmful to human health and the environment, and can be costly to produce and apply. Thus, recent developments in the field have focused on developing biocontrol or naturally derived treatments to inhibit fungal pathogens.

In general, using biocontrol agents against plant pathogens is preferred over using commercial chemicals and can be both economically efficient and more environmentally sound.

Thus, biocontrol agents for use against soil and air-borne fungal pathogens solving the aforementioned problems are desired.

SUMMARY

The biocontrol agents for use against soil and air-borne fungal pathogens may include a mixture of at least three *Trichoderma* species, including *Trichoderma harzianum*, *Trichoderma longibrachiatum*, and *Trichoderma asperellum*. This mixture of *Trichoderma* isolates exhibits activity showing that it may effectively control plant pathogens. The biocontrol agent for use against soil and air-borne fungal pathogens may be formulated as a wettable powder. The biocontrol agent may be used to treat or prevent infection of date palms with *Thielaviopsis punctulata*, commonly referred to as black scorch disease. The biocontrol agent may also be used in the treatment or prevention of infection of cucumbers with *Rhizoctonia solanii*, commonly referred to as damping off disease.

These and other features of the present subject matter will become readily apparent upon further review of the following specification.

DETAILED DESCRIPTION OF THE PREFERRED EMBODIMENTS

The biocontrol agents for use against soil and air-borne fungal pathogens may include a mixture of at least three *Trichoderma* species, including *Trichoderma harzianum*, *Trichoderma longibrachiatum*, and *Trichoderma asperellum*. This mixture of *Trichoderma* isolates may be effective in controlling plant pathogens. The biocontrol agent for use against soil and air-borne fungal pathogens may be formulated as a wettable powder. The biocontrol agent may be used in the treatment or prevention of infection of date palms with *Thielaviopsis punctulata*. The biocontrol agent may also be used in the treatment or prevention of infection of cucumbers with *Rhizoctonia solanii*.

Throughout this application, the term "about" may be used to indicate that a value includes the standard deviation of error for the composition, device or method being employed to determine the value.

The use of the term "or" in the specification and claim(s) is used to mean "and/or" unless explicitly indicated to refer to alternatives only or that the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In certain cases, the term "comprising" may be replaced with "consisting essentially of" or "consisting of."

The use of the word "a" or "an" when used herein in conjunction with the term "comprising" in the claims and/or the specification may mean "one," but it is also consistent with the meaning of "one or more," "at least one," and "one or more than one."

In the various embodiments described herein, the biocontrol agents may be effective in controlling against plant pathogens; they may be formulated as a wettable powder; they may be used in the treatment or prevention of infection of date palms with *Thielaviopsis punctulata*; and/or they may be used in the treatment or prevention of infection of cucumbers with *Rhizoctonia solanii*.

The biocontrol agents were developed by first isolating numerous *Trichoderma* isolates from field surveys in Saudi Arabia. Strains of a variety of *Trichoderma* species were selected from the rhizosphere of healthy date palm plants and identified using morphological and molecular approaches. The isolates were selected in this way in part to ensure that they were adapted to the local agro-climactic conditions and were thus particularly well-suited to biocontrol applications in the Gulf Coast Cooperative (GCC) region and in regions with similar climatic conditions.

The *Trichoderma* isolates were identified using PCR and sequencing of the partial regions of the ITS. Five isolates were identified representing three *Trichoderma* species: a *T. longibrachiatum* isolate, two *T. asperellum* isolates, and two *T. harzianum* isolates. The efficacy of each of these isolates, and of a combination of isolates from *T. longibrachiatum*, *T. asperellum*, *T. harzianum*, as biocontrol agents were tested. Both the individual isolates and the combination of isolates demonstrated ability to inhibit disease severity of *T. punctulata* in date palm and *R. solanii* in cucumber.

In an embodiment, biocontrol agents may be formulated by growing mycelial disks of one or more *Trichoderma* species in potato dextrose broth, collecting the growing mycelium, and homogenizing the mycelium in a blender. The homogenized mycelium may then be mixed with talc powder and air-dried to produce a wettable powder. The wettable powder may then be used as a biopesticide composition by dissolving the wettable powder in water. In a further embodiment, two mycelial discs of each of three *Trichoderma* isolates may be grown in 1 L of potato dextrose broth (PDB) in a flask at 25° C. for 14 days. Growing mycelium may be collected and homogenized in the blender to create a green slurry. The slurry may be mixed with sterilized talc powder at a 1:1 ratio and the resulting mixtures of each of the three isolates may be blended together and air-dried under sterile conditions to produce a wettable powder. The resulting biopesticide compositions may be stored in polypropylene bags until further use. The wettable powder may be dissolved in water at a ratio of 10 g powder per liter of water for use in biological control applications.

In an embodiment, biocontrol agents may be formulated including specific strains of *T. harzianum* (TH1-MT530123), *T. longbrachiatum* (TL1-MT520646), and *T. asperellum* (TA2-MT341772). In a further embodiment, these strains may be identified by the presence of specific genomic sequences in the ITS region as follows. The sequence of TL1 is:

TL1:
(SEQ ID NO: 1)
CCCAAACCCCAATGTGAACGTTACCAATCTGTTGCCTCGGCGGGATTCT

CTTGCCCCGGGCGCGTCGCAGCCCCGGATCCCATGGCGCCCGCCGGAGG

ACCAACTCCAAACTCTTTTTTCTCTCCGTCGCGGCTCCCGTCGCGGCTC

TGTTTTATTTTTGCTCTGAGCCTTTCTCGGCGACCCTAGCGGGCGTCTC

GAAAATGAATCAAAACTTTCAACAACGGATCTCTTGGTTCTGGCATCGA

TGAAGAACGCAGCGAAATGCGATAAGTAATGTGAATTGCAGAATTCAGT

GAATCATCGAATCTTTGAACGCACATTGCGCCCGCCAGTATTCTGGCGG

GCATGCCTGTCCGAGCGTCATTTCAACCCTCGAACCCCTCCGGGGGTC

GGCGTTGGGGATCGGCC.

The sequence of TA2 is:

TA2:
(SEQ ID NO: 3)
TCCGTAGGTGAACCTGCGGAGGGATCATTACCGAGTTTACAACTCCCAA

ACCCAATGTGAACGTTACCAAACTGTTGCCTCGGCGGGGTCACGCCCCG

GGTGCGTCGCAGCCCCGGAACCAGGCGCCCGCCGGAGGAACCAACCAAA

CTCTTTCTGTAGTCCCCTCGCGGACGTATTTCTTTACAGCTCTGAGCAA

AAATTCAAAATGAATCAAAACTTTCAACAACGGATCTCTTGGTTCTGGC

ATCGATGAAGAACGCAGCGAAATGCGATAAGTAATGTGAATTGCAGAAT

TCAGTGAATCATCGAATCTTTGAACGCACATTGCGCCCGCCAGTATTCT

GGCGGGCATGCCTGTCCGAGCGTCATTTCAACCCTCGAACCCCTCCGGG

GGATCGGCGTTGGGGATCGGGACCCCTCACACGGGTGCCGGCCCCTAAA

TACAGTGGCGGTCTCGCCGCAGCCTCTCCTGCGCAGTAGTTTGCACAAC

TCGCACCGGGAGCGCGGCGCGTCCACGTCCGTAAAACACCCAACTTTCT

GAAATGTTGACCTCGGATCAGGTAGGAATACCCGCTGAACTTAAGCATA

TCAATAA.

The sequence of TH1 is:

TH1:
(SEQ ID NO: 4)
GGGATCATTACCGAGTTTACAACTCCCAAACCCAATGTGAACGTTACCA

AACTGTTGCCTCGGCGGGATCTCTGCCCCGGGTGCGTCGCAGCCCCGGA

CCAAGGCGCCCGCCGGAGGACCAACCAAAACTCTTATTGTATACCCCCT

CGCGGGTTTTTTTTATAATCTGAGCCTTCTCGGCGCCTCTCGTAGGCGT

TTCGAAAATGAATCAAAACTTTCAACAACGGATCTCTTGGTTCTGGCAT

CGATGAAGAACGCAGCGAAATGCGATAAGTAATGTGAATTGCAGAATTC

AGTGAATCATCGAATCTTTGAACGCACATTGCGCCCGCCAGTATTCTGG

CGGGCATGCCTGTCCGAGCGTCATTTCAACCCTCGAACCCCTCCGGGGG

GTCGGCGTTGGGGATCGGCCCTGCCTTGGCGGTGGCCGTCTCCGAAATA

CAGTGGCGGTCTCGCCGCAGCCTCTCCTGCGCAGTAGTTTGCACACTCG

CATCGGGAGCGCGGCGCGTCCACAGCCGTTAAACACCCAACTTCTGAA.

The biocontrol agents for use against soil and air-borne fungal pathogens will be better understood with reference to the following examples.

Example 1

Isolation and Purification of *Trichoderma* Isolates

The Dilution Plate Method (DPM) was used for the isolation of *Trichoderma* species. Soil and rhizosphere samples were taken by carefully uprooting plants to obtain intact root systems. The root systems were shaken gently to remove adhering soil particles and transferred to a wide mouth reagent bottle containing 99 ml sterile distilled water and 1 g soil. *Trichoderma* Selective Medium (TSM) was used for isolation of *Trichoderma* isolates according to the methods described by Elad et al. (Y. Elad et al., "Biological control of *Rhizoctonia solani* by *Trichoderma harzianum* in carnation," Plant Dis., 65: 675-677 (1981)).

Briefly, a diluted spore suspension of each isolate of the sporulating fungi was prepared by washing a pure culture of the fungus with 50 ml of sterilized distilled water. The spore suspensions were poured into Petri dishes over solid transparent agar medium. Single spores were selected and marked with a grid drawn on the base of each Petri dish under a compound microscope. The plates were incubated until germ tubes became visible. The marked spores were then subcultured onto fresh potato dextrose agar (PDA) using a flatted end needle. The inoculated plates were incubated at 25° C. for 3-7 days and were examined daily to observe fungal growth.

After seven days, the developed fungal colonies were examined under a compound microscope and colonies were identified using the morphological and microscopic characteristics. Obtained isolates of *Trichoderma* spp. were divided based on the growth rate characteristics and sporulation capacity and five fungal isolates were selected for Sanger sequencing.

Total genomic DNA was isolated from each selected fungal isolate using Qiagen DNeasy Plant Mini Kit according to the manufacturer's instructions. PCR was performed to amplify the entire sequence of the internal transcribed spacer (ITS), one (ITS1), and ITS2 regions using an ITS-specific primer pair ITS4/ITS5, as previously described by White et al. (T. J. White et al., "Amplification and direct sequencing of fungal ribosomal RNA genes for phylogenetics. PCR protocols: a guide to methods and applications," 18(1): pp. 315-322 (1990)). PCR products were purified and subsequently sequenced in both directions. The obtained nucleotide sequences were compared with available sequences in the NCBI GenBank database to identify the *Trichoderma* isolates.

The nucleotide sequences of the ITS region of each *Trichoderma* isolate were matched against existing GenBank sequences to determine the identities of each isolate. Isolate TL1 was 100% identical to *T. longibrachiatum* (MT520646). Isolates TA1 and TA2 were 100% identical to *T. asperellum* (MH215549 and MT341772, respectively), and isolates TH1 and TH2 were 100% identical to *T. harzianum* (MT530123 and MF780869, respectively).

The genomic sequence of the ITS region of isolate TL1 was:

(SEQ ID NO: 1)
CCCAAACCCCAATGTGAACGTTACCAATCTGTTGCCTCGGCGGGATTCT

CTTGCCCCGGGCGCGTCGCAGCCCCGGATCCCATGGCGCCCGCCGGAGG

ACCAACTCCAAACTCTTTTTTCTCTCCGTCGCGGCTCCCGTCGCGGCTC

TGTTTTATTTTTGCTCTGAGCCTTTCTCGGCGACCCTAGCGGGCGTCTC

GAAAATGAATCAAAACTTTCAACAACGGATCTCTTGGTTCTGGCATCGA

TGAAGAACGCAGCGAAATGCGATAAGTAATGTGAATTGCAGAATTCAGT

GAATCATCGAATCTTTGAACGCACATTGCGCCCGCCAGTATTCTGGCGG

GCATGCCTGTCCGAGCGTCATTTCAACCCTCGAACCCCTCCGGGGGTC

GGCGTTGGGGATCGGCC.

The genomic sequence of the ITS region of isolate TA1 was:

(SEQ ID NO: 2)
CATTACCGAGTTTACAACTCCCAAACCCAATGTGAACGTTACCAAACTG

TTGCCTCGGCGGGTCACGCCCCGGGTGCGTCGCAGCCCCGGAACCAGG

CGCCCGCCGGAGGAACCAACCAAACTCTTTCTGTAGTCCCCTCGCGGAC

GTATTTCTTTACAGCTCTGAGCAAAAATTCAAATGAATCAAAACTTTC

AACAACGGATCTCTTGGTTCTGGCATCGATGAAGAACGCAGCGAAATGC

GATAAGTAATGTGAATTGCAGAATTCAGTGAATCATCGAATCTTTGAAC

GCACATTGCGCCCGCCAGTATTCTGGCGGGCATGCCTGTCCGAGCGTCA

TTTCAACCCTCGAACCCCTCCGGGGGATCGGCGTTGGGGATCGGGACCC

CTCACACGGGTGCCGGCCCCTAAATACAGTGGCGGTCTCGCCGCAGCCT

CTCCTGCGCAGTAGTTTGCACAACTCGCACCGGGAGCGCGGCGCGTCCA

CGTCCGTAAAACACCCAACTTTCTGAAATGTTGACCTCGGATCAGGTAG

GAATACCCGCTGAACTTAAGC ATATCATAA.

The genomic sequence of the ITS region of TA2 was:

(SEQ ID NO: 3)
TCCGTAGGTGAACCTGCGGAGGGATCATTACCGAGTTTACAACTCCCAA

ACCCAATGTGAACGTTACCAAACTGTTGCCTCGGCGGGGTCACGCCCCG

GGTGCGTCGCAGCCCCGGAACCAGGCGCCCGCCGGAGGAACCAACCAAA

CTCTTTCTGTAGTCCCCTCGCGGACGTATTTCTTTACAGCTCTGAGCAA

AAATTCAAAATGAATCAAAACTTTCAACAACGGATCTCTTGGTTCTGGC

ATCGATGAAGAACGCAGCGAAATGCGATAAGTAATGTGAATTGCAGAAT

TCAGTGAATCATCGAATCTTTGAACGCACATTGCGCCCGCCAGTATTCT

GGCGGGCATGCCTGTCCGAGCGTCATTTCAACCCTCGAACCCCTCCGGG

GATCGGCGTTGGGGATCGGGACCCCTCACACGGGTGCCGGCCCCTAAA

TACAGTGGCGGTCTCGCCGCAGCCTCTCCTGCGCAGTAGTTTGCACAAC

TCGCACCGGGAGCGCGGCGCGTCCACGTCCGTAAAACACCCAACTTTCT

GAAATGTTGACCTCGGATCAGGTAGGAATACCCGCTGAACTTAAGCATA

TCAATAA.

The genomic sequence of the ITS region of TH1 was:

(SEQ ID NO: 4)
GGGATCATTACCGAGTTTACAACTCCCAAACCCAATGTGAACGTTACCA

AACTGTTGCCTCGGCGGGATCTCTGCCCCGGGTGCGTCGCAGCCCCGGA

CCAAGGCGCCCGCCGGAGGACCAACCAAAACTCTTATTGTATACCCCCT

CGCGGGTTTTTTTTATAATCTGAGCCTTCTCGGCGCCTCTCGTAGGCGT

TTCGAAAATGAATCAAAACTTTCAACAACGGATCTCTTGGTTCTGGCAT

CGATGAAGAACGCAGCGAAATGCGATAAGTAATGTGAATTGCAGAATTC

AGTGAATCATCGAATCTTTGAACGCACATTGCGCCCGCCAGTATTCTGG

CGGGCATGCCTGTCCGAGCGTCATTTCAACCCTCGAACCCCTCCGGGGG

GTCGGCGTTGGGGATCGGCCCTGCCTTGGCGGTGGCCGTCTCCGAAATA

CAGTGGCGGTCTCGCCGCAGCCTCTCCTGCGCAGTAGTTTGCACACTCG

CATCGGGAGCGCGGCGCGTCCACAGCCGTTAAACACCCAACTTCTGAA.

The genomic sequence of the ITS region of TH2 was:

(SEQ ID NO: 5)
GGAAGTAAAAGTCGTAACAAGGTCTCCGTTGGTGAACCAGCGGAGGGAT

CATTACCGAGTTTACAACTCCCAAACCCAATGTGAACGTTACCAAACTG

TTGCCTCGGCGGGATCTCTGCCCCGGGTGCGTCGCAGCCCCGGACCAAG

GCGCCCGCCGGAGGACCAACCAAAACTCTTATTGTATACCCCCTCGCGG

GTTTTTTTTATAATCTGAGCCTTCTCGGCGCCTCTCGTAGGCGTTTCGA

AAATGAATCAAAACTTTCAACAACGGATCTCTTGGTTCTGGCATCGATG

AAGAACGCAGCGAAATGCGATAAGTAATGTGAATTGCAGAATTCAGTGA

ATCATCGAATCTTTGAACGCACATTGCGCCCGCCAGTATTCTGGCGGGC

ATGCCTGTCCGAGCGTCATTTCAACCCTCGAACCCCTCCGGGGGGTCGG

CGTTGGGGATCGGCCCTGCCTTGGCGGTGGCCGTCTCCGAAATACAGTG

GCGGTCTCGCCGCAGCCTCTCCTGCGCAGTAGTTTGCACACTCGCATCG

GGAGCGCGGCGCGTCCACAGCCGTTAAACACCCAACTTCTGAAATGTTG

ACCTCGGATCAGGTAGGAATACCCGCTGAACTTAAGCATATC AATAAG

CGGAGGA.

Example 2

In Vitro Antagonistic Evaluation of *Trichoderma* Isolates Against *T. punctulata* and *R. solani*

The antagonistic ability of the five *Trichoderma* isolates belonging to *T. harzianum* (TH1 and TH2), *T. longibrachiatum* (TL1), and *T. asperellum* (TA1 and TA2) were tested against three *T. punctulata* isolates (TP1, TP2, and TP3) and two *R. solani* isolates (RS1 and RS2) in dual culture. One week old potato dextrose agar (PDA) cultures of *Trichoderma* isolates and both pathogens were used as a source of inoculum in 90 mm petri plates. A disk of each *Trichoderma* isolated (4 mm diameter) was placed 20 mm from the edge of the PDA plates. A disk of a pathogen was then placed 50 mm away from the *Trichoderma* isolate disk. Cultures were then incubated in the dark at 25° C. until the pathogen spread to completely cover the check plates. The inhibition of each pathogen's growth was calculated as an index of antagonistic ability of the respective *Trichoderma* isolates according to the following Formula 1:

$$\% \text{ Inhibition} = \frac{R_1 - R_2}{R_1} \times 100,$$

wherein $R_1$ is the maximum radius of the pathogen colony and $R_2$ is the radius of the pathogen colony opposite to the *Trichoderma* colony.

Example 3

Formulation of Working Biopesticides

Based upon the results of Example 2, *T. harzianum* (TH1), *T. longbrachiatum* (TL1), and *T. asperellum* (TA2) strains were chosen for formulation of a biopesticide. Two mycelial discs of each *Trichoderma* isolated were grown in 1 L of potato dextrose broth (PDB) in a flask at 25° C. for 14 days. Growing mycelium was then collected and homogenized in the blender to create a green slurry. The slurry was then mixed with sterilized talc powder at a 1:1 ratio and the resulting mixtures of each of the three isolates were then blended together and air-dried under sterile conditions to produce a wettable powder. The resulting biopesticide compositions (both individual isolates and the combination of all three isolates) were stored in polypropylene bags until further use. The wettable powder was then dissolved in water at a ratio of 10 g powder per liter water for use in biological control applications.

Example 4

Evaluation of Biopesticides against *Thielaviopsis punctulata* and *Rhizoctonia solani*

Evaluation of the biopesticide compositions produced according to Example 3 against *T. punctulata* was tested as follows. Disease severity was evaluated on leaves and root tissues of date palm cv Khalas seedlings. A ten-day old culture of a *T. punctulata* isolate (TP1) grown on corn meal agar was inoculated on a wounded part at the leaf base of the seedlings. Plastic pots filled with sterilized soil were also inoculated by drenching 50 ml of potato broth medium with spore suspension at $1 \times 10^7$ conidia per ml. Following leaf inoculation and soil infestation, formulated biopesticide (produced according to Example 3) was sprayed at a rate of 10 g/L and a further 50 ml of formulated biopesticide was added to the infested soil.

Evaluation of the biopesticide composition produced according to Example 3 against cucumber damping off was tested as follows. Sterilized soil was inoculated with 3% of a 15-day old culture of *R. solani* (RS1) grown on corn meal sand medium, at a rate of 2-5 g of corn meal to 98-95 g sand in 250 ml glass bottles. Control seedlings were sprayed with sterilized water only. Lesion development was measured, and root rot and wilt symptoms were observed 4 weeks post treatment. Five replicates were used for each treatment and the experiments were repeated three times.

Pathogenicity and the effect of the formulated biopesticide were calculated using a completely randomized design. Analysis of variance (ANOVA) and least significant difference (LSD) tests were conducted to determine statistical significance (P<0.05). All statistical analysis was carried out using SAS/STAT® 9.3 software (SAS, USA).

The tested biopesticides of *Trichoderma* spp. showed significant antagonistic activity against all three *T. punctulata* isolates (TP1, TP2, TP3). The results demonstrated an inhibition percentage ranging between 56.89-62.44, 56.89-63.33, and 57.11-61.11% against TP1, TP2, and TP3 isolates, respectively (see Tables 1A-1C, below). The most effective isolate against TP1 was *T. longibrachium*, while *T. asperellum* had the highest inhibition rate on isolate TP2. The mixture of all three isolates demonstrated an inhibition ranging from 58.22% to 61.11%.

TABLE 1A

Antagonistic Evaluation of Dual Culture between *Trichoderma* spp. and *T. punctulata*

| | TP1 | |
| --- | --- | --- |
| | Growth mm | Inhibition % |
| *T. longibrachiatum* (TL 1) | 33.80 ± 2.68 | 62.44 |
| *T. asperellum* (TA1) | 38.20 ± 1.64 | 57.56 |
| *T. asperellum* (TA2) | 37.60 ± 2.30 | 58.22 |
| *T. harzianum* (TH1) | 37.20 ± 0.84 | 58.67 |
| *T. harzianum* (TH2) | 38.80 ± 2.17 | 56.89 |
| Control | 90.00 ± 00 | 0.00 |

TABLE 1B

Antagonistic Evaluation of Dual Culture between *Trichoderma* spp. and *T. punctulata*

| | TP2 | |
| --- | --- | --- |
| | Growth mm | Inhibition % |
| *T. longibrachiatum* (TL 1) | 38.80 ± 1.10 | 56.89 |
| *T. asperellum* (TA1) | 35.60 ± 1.82 | 60.44 |
| *T. asperellum* (TA2) | 32.00 ± 2.12 | 64.44 |
| *T. harzianum* (TH1) | 33.60 ± 1.34 | 62.67 |
| *T. harzianum* (TH2) | 33.00 ± 1.73 | 63.33 |
| Control | 90.00 ± 00 | 0.00 |

TABLE 1C

Antagonistic Evaluation of Dual Culture between *Trichoderma* spp. and *T. punctulata*

| | TP3 | |
| --- | --- | --- |
| | Growth mm | Inhibition % |
| *T. longibrachiatum* (TL 1) | 35.40 ± 1.67 | 60.67 |
| *T. asperellum* (TA1) | 35.00 ± 2.00 | 61.11 |
| *T. asperellum* (TA2) | 35.20 ± 1.30 | 60.89 |
| *T. harzianum* (TH1) | 38.60 ± 0.89 | 57.11 |
| *T. harzianum* (TH2) | 37.60 ± 1.95 | 58.22 |
| Control | 90.00 ± 00 | 0.00 |

TABLE 2A

Antagonistic Evaluation of Dual Culture between *Trichoderma* spp. and *R. Solani*

| | Isolate 1 | |
|---|---|---|
| | Radial Growth (mm) | Inhibition (%) |
| *T. longibrachiatum* (TL1) | 45.80 ± 2.387 | 49.1 |
| *T. asperellum* (TA1) | 22.40 ± 2.510 | 75.1 |
| *T. asperellum* (TA2) | 25.80 ± 2.280 | 71.3 |
| *T. harzianum* (TH1) | 46.00 ± 1.225 | 48.9 |
| *T. harzianum* (TH2) | 27.80 ± 2.280 | 69.1 |
| Control | 90.00 ± 0.000 | 0.0 |

TABLE 2B

Antagonistic Evaluation of Dual Culture between *Trichoderma* spp. and *R. Solani*

| | Isolate 2 | |
|---|---|---|
| | Radial Growth (mm) | Inhibition (%) |
| *T. longibrachiatum* (TL1) | 48.8 ± 2.588 | 45.8 |
| *T. asperellum* (TA1) | 18.6 ± 1.42 | 79.3 |
| *T. asperellum* (TA2) | 26.2 ± 1.643 | 70.9 |
| *T. harzianum* (TH1) | 40.8 ± 1.789 | 54.7 |
| *T. harzianum* (TH2) | 28.8 ± 1.483 | 68.0 |
| Control | 90.00 ± 0.000 | 0.00 |

The tested biopesticides of *Trichoderma* spp. also showed significant antagonistic activity against *R. solani*. The results demonstrated an inhibition percentage ranging between 49.1-75.1% and 54.8-79.3% against two respective isolates of *R. solani* (see Tables 2A-2B, above).

An in vivo analysis of the antagonistic effect of the tested biopesticides against *T. punctulata* in date palm and against *R. solani* in cucumbers was also performed under greenhouse conditions. This test demonstrated that the biopesticides demonstrated inhibition of black scorch disease in the date palm 60.98% of the time and damping off in cucumbers 64.68% of the time.

It is to be understood that the biocontrol agents for use against soil and air-borne fungal pathogens is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A biocontrol agent for use against soil or airborne pathogens, consisting of a wettable powder including:
   at least one strain of *Trichoderma harzianum*,
   at least one strain of *Trichoderma longibrachiatum*; and
   at least one strain of *Trichoderma asperellum*.

2. The biocontrol agent as recited in claim 1, wherein said at least one strain of *Trichoderma harzianum* includes the genomic ITS sequence of SEQ ID NO: 4.

3. The biocontrol agent as recited in claim 1, wherein said at least one strain of *Trichoderma longibrachiatum* includes the genomic ITS sequence of SEQ ID NO: 1.

4. The biocontrol agent as recited in claim 1, wherein said at least one strain of *Trichoderma asperellum* includes the genomic ITS sequence of SEQ ID NO: 3.

5. A method of inhibiting a plant disease, comprising administering a biocontrol agent to a plant in need thereof, the biocontrol agent consisting of a wettable powder including:

at least one strain of *Trichoderma harzianum,* at least one strain of *Trichoderma longibrachiatum*; and at least one strain of *Trichoderma asperellum.*

6. The method of inhibiting a plant disease as recited in claim 5, wherein said at least one strain of *Trichoderma harzianum* includes the genomic ITS sequence of SEQ ID NO: 4.

7. The method of inhibiting a plant disease as recited in claim 5, wherein said at least one strain of *Trichoderma longibrachiatum* includes the genomic ITS sequence of SEQ ID NO: 1.

8. The method of inhibiting a plant disease as recited in claim 5, wherein said at least one strain of *Trichoderma asperellum* includes the genomic ITS sequence of SEQ ID NO: 3.

9. The method of inhibiting a plant disease as recited in claim 5, wherein the plant is a cucumber.

10. The method of inhibiting a plant disease as recited in claim 9, wherein the plant disease is *Rhizoctonia solanii.*

11. The method of inhibiting a plant disease as recited in claim 5, wherein the plant is a date palm.

12. The method of inhibiting a plant disease as recited in claim 11, wherein the plant disease is *Thielaviopsis punctulata.*

13. The method of inhibiting a plant disease as recited in claim 5, wherein the biocontrol agent is sprayed on the leaves of the plant in need thereof.

14. The method of inhibiting a plant disease as recited in claim 5, wherein the biocontrol agent is administered to soil in which the plant in need thereof is growing.

15. A method of producing the biocontrol agent of claim 1, comprising the steps of:

(a) growing at least one *Trichoderma* strain in potato dextrose broth to obtain growing mycelium;

(b) collecting growing mycelium and homogenizing the growing mycelium to obtain a slurry;
(c) mixing the slurry with sterilized talc powder at a 1:1 ratio to obtain a first mixture;
(d) repeating steps (a)-(c) for at least two additional *Trichoderma* strains to obtain two additional mixtures; and
(e) blending and air-drying the first mixture and the two additional mixtures to obtain a wettable powder for use as a biocontrol agent.

16. The method of producing a biocontrol agent as recited in claim 15, wherein one of the *Trichoderma* strains is *Trichoderma harzianum*, including the genomic ITS sequence of SEQ ID NO: 4.

17. The method of producing a biocontrol agent as recited in claim 15, wherein one of the *Trichoderma* strains isolates is *Trichoderma longibrachiatum*, including the genomic ITS sequence of SEQ ID NO: 1.

18. The method of producing a biocontrol agent as recited in claim 15, wherein one of the *Trichoderma* strains is *Trichoderma asperellum*, including the genomic ITS sequence of SEQ ID NO: 3.

* * * * *